(12) United States Patent
Froloff (10) Patent No.: US 10,342,433 B2
(45) Date of Patent: Jul. 9, 2019

(54) INSITU DIAGNOSTIC TOOL FOR DIGITAL PATHOLOGY

(71) Applicant: Walt Froloff, Aptos, CA (US)

(72) Inventor: Walt Froloff, Aptos, CA (US)

( * ) Notice: Subject to any disclaimer, the term of this patent is extended or adjusted under 35 U.S.C. 154(b) by 702 days.

(21) Appl. No.: 14/745,893

(22) Filed: Jun. 22, 2015

(65) Prior Publication Data

US 2016/0367148 A1    Dec. 22, 2016

(51) Int. Cl.
*A61B 1/00* (2006.01)
*A61B 5/00* (2006.01)
*A61B 1/303* (2006.01)

(52) U.S. Cl.
CPC .......... *A61B 5/0084* (2013.01); *A61B 1/0005* (2013.01); *A61B 1/00009* (2013.01); *A61B 1/303* (2013.01); *A61B 5/4331* (2013.01); *A61B 2562/0242* (2013.01)

(58) Field of Classification Search
CPC . A61B 5/0084; A61B 1/00009; A61B 1/0005; A61B 1/303; A61B 5/4331; A61B 2562/0242
See application file for complete search history.

(56) References Cited

U.S. PATENT DOCUMENTS

| | | | | |
|---|---|---|---|---|
| 4,820,015 A * | 4/1989 | Mogi | .......... | G02B 6/0008 385/115 |
| 6,277,067 B1 * | 8/2001 | Blair | .......... | A61B 1/00041 348/77 |
| 6,346,086 B1 * | 2/2002 | Maksem | ......... | A61B 10/0291 600/569 |
| 2001/0023321 A1 * | 9/2001 | Gombrich | ......... | A61B 10/0291 600/562 |
| 2014/0142433 A1 * | 5/2014 | Greenstein | ......... | A61B 1/042 600/473 |

OTHER PUBLICATIONS

Quinn et al. (2012 PLOS One 7:e44924 6pages) (Year: 2012).*

* cited by examiner

*Primary Examiner* — Tse W Chen
*Assistant Examiner* — Patrick M Mehl
(74) *Attorney, Agent, or Firm* — Walt Froloff (57) ABSTRACT

An in vivo and insitu diagnostic and light therapeutic tool for the Pap test having a cavity fitting housing with an optical and digital magnification path coupled to image detecting sensor logic. The tool has an optical scraper stem mechanically controlled and extendable from within the housing, the stem having at least one fiber optical channel for selected frequency and wavelength light various light sources, an optical scraper slide component optically coupled to the scraper fiber optic channel stem distal end, channeling light from the housing to the scraper slide normal axis surface for illumination penetrating a specimen sample for optical imaging into an optical microscopy magnification path axis whereby micrograph image from in vivo Pap tests can be accomplished and resulting image micrographs programmatically identified and verified in situ in real-time.

10 Claims, 10 Drawing Sheets

INSITU DIAGNOSTIC TOOL FOR DIGITAL PATHOLOGY

BACKGROUND

Field of the Invention

The present invention relates generally to the field of in-situ real-time invivo diagnostic tools, and specifically to real-time result Pap Smear Tests.

Background Description

There have been successful attempts to develop automated, computer Pap image analysis systems for screening. A recent NHS Health technology appraisal concluded that the general case for automated image analysis had probably been made. Automation may improve sensitivity and reduce unsatisfactory specimens. Two systems have been approved by the PDA and function In high-volume reference laboratories, with human oversight. While this is a good step in the right direction, what is needed is automation of the automation, the entire process and not just pieces. The Papanicolaou test AKA Pap test or Pap smear, cervical smear, or smear test is a method of cervical screening used to detect potentially pre-cancerous and cancerous processes in the endocervical canal, "transformation zone", of the female reproductive system. Unusual findings are often followed up by more sensitive diagnostic procedures, and, if warranted, interventions that aim to prevent progression to cervical cancer Pap smears are a routine operation and needed by 100 million women in the U.S. each year. The minimum cost for a simple test with no complications is in the range of $30. This represents a minimum of a $3 Billion health care market for a simple Pap smear test alone.

The Pap smear process includes scheduled doctor intensive exam, in which a speculum is used manually and diagnostics follows but also done manually and may take weeks of time to schedule and complete. A smear is then sent to a lab for a specialist to analyze for pre-cancerous and cancerous cells. Other bacteria, fungus, virus or anomalies are screened and identified by inspection by a specialist. The smear is obtained manually via a tool called a speculum.

The best-known speculum is the bivalved vaginal speculum but a cylindrical-shaped speculum, introduced in 2001, the dilating vaginal speculum also known as the Veda-scope is also used, which inflates the vagina with filtered air. The device has two main functions: a) to take a normal PAP smear with a cervical brush or a cytology brush; and b) as an internal colposcope so that the operator can pivot the Veda-scope to view any part of the vagina barrel and cervix facilitated by an internal light source that can illuminate the vaginal wall and cervix with multi-colored light filters, which can detect pre-cancerous cells with the aid of acetic acid solution and solution. It also has a facility to attach a digital camera for viewing and recording.

Currently inspection of samples taken from a Pap test include Endocervical adenocarcinoma, Candide organisms, viral cytopathic effect consistent with herpes simplex virus, normal squamous epithelial cells in premenopausal women, atrophic squamous cells in postmenopausal women, the cytoplasms of squamous epithelial cells melted out Infestation by *Trichomonas vaginalis*, obviously atypical cell, HPV legions and other anomalous or symptomatic characteristics are found by inspection of Pap smears. Identification is through manual sampling and specialist inspection. Manual inspection and analysis of any of these have known and well used treatments. However human inspection and lab analysis is fallible, time consuming, and costly. Many of these can be discovered by image processing and comparison with standard known sample images in minutes.

The microbial offending life may reside inside of tissue on or below the tissue surface. Currently "scraping" instruments are used to make microscope slide samples which can be analyzed. What is needed are ways to find the offending organisms at what ever tissue level they reside without the use of "scraping" for lab test slides for microscopy scrutiny.

In the United States, a pap test itself costs $20 Co $30, but the costs for pap test visits can cost over $1,000, largely because additional tests are added that may or may slot be necessary, depending on the Pap smear test results. Results on occasion find human papillomavirus (HPV), a DNA virus which establish productive infections only in mucous membranes. Most HPV infections are subclinical and will cause no physical symptoms; however, in some people infections may cause benign squamous cell papilloma, or cancers of the cervix, vulva, vagina and other organs with mucous membranes. Out of the over a hundred variants. HPV16 and HPV18 are known to cause around 70% of cervical cancer cases. Surgical removal, topical creams and laser are the three methods currently used to excise these cancer agents. But Pap smears are the best and most used method for early detection of harmful HPV, followed by treatment if the HPV precancerous squamous cell is found. What is needed is a Pap test that give a woman all the results all at one time, so that follow-on procedures can be established with out undue time and cost escalation.

Recent advancements in photonic microscopy diagnostics, detection and imaging technologies have made inroads into computer image processing and automation. Theses are emerging technologies which can replace outdated medical diagnostic and treatment processes. Many medical procedures are time consuming, logistically challenging for medical staff and doctors driving up medical and health care costs. In addition many ailments and maladies can be diagnosed, identified and remedied, using similar tools, techniques and procedures. Technology used in analyzing tissue, assay and blood samples in the medical arena are growing, but they are not well integrated. Technology fiber optics and photonics, endoscopes and microscopes, instruments used to examine the interior cavity of the body or organ and other process require the obtaining of samples manually, physical examination of samples at laboratories for manual inspection by a specialist. Much of this labor can be integrated through digital imaging, software, optical microscopy, LED and laser technology.

Laparoscopy

While laparoscopy with the aid of a camera can either be used to inspect and diagnose a condition or to perform surgery, Pap smear samples and micrograph images are still done the old fashion way, by scraper. By and large laparoscopes are rigid endoscopes. The rigidness is required in clinical practice. The rod lens based laparoscopes are highly dominant in practice, due to their optical resolution of typically 50 µm, dependant on the aperture size used in the objective lens, and the image quality can be better than the digital cameras if necessary. The 1000× magnification is not possible with laparoscopes. What is needed are higher resolution and magnification laparoscopy.

Photonics and Microscopy

Digital and optical microscopy have also seen tremendous inroads in the medical fields. However a multidisciplinary approach involving the collaboration between clinicians and technology developers is necessary for the implementation of new medical devices. Change and adoption are faster when the antiquated manual process methods prove too expensive on patients as well as medical and health care staff. What is needed are ways to obtain and analyze bio-samples more quickly using faster developed technology programmatically.

SUMMARY

The present invention discloses a removable insitu in vivo diagnostic tool for the Pap test built into a human cavity fitting housing having an optical and digital magnification path coupled to image detecting sensor logic. The tool has an optical scraper stem mechanically controlled and extendable from within the housing, the stem having at least one fiber optical channel for conducting selected frequency and wavelength light from single frequency or tunable light sources, an optical scraper slide component optically coupled to the scraper fiber optic channel stem distal end, channeling light from the housing to the scraper slide normal axis surface for illumination penetrating a specimen sample for optical imaging into an optical microscopy magnification path axis. The optical microscopy magnification path focusing microgragh images on a digital CCD or CMOS detector which has the image detector electronically coupled to electronic imaging for programmatic processing and display of micrograph images, and the image processing coupled to logic for identification of known harmful or precursors to harmful bio-entities in the micrograph image whereby Pap tests can be accomplished and resulting image micrographs programmatically identified and verified in situ in vivo in real-time.

BRIEF DESCRIPTION OF DRAWINGS

Specific embodiments of the invention will be described in detail with preference to the following figures.

DETAILED DESCRIPTION

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

OBJECTS AND ADVANTAGES

An object of the invention is to discover vaginal cavity and cervix any harmful pre-cancerous or cancerous agents from a purely optical insitu method.

Another object if the invention is to create sample slides in vivo with all of the microscopy components necessary for high magnification image processing.

Another object of the invention is to reduce cost and time for discovering female ailments originating in the vagina and cervix.

Another object of the invention is to automate the diagnosis of Pap smears from taking of the bio-sample to identification and certification of the potential harm for remedial action.

Yet another object of the invention is to create vaginal/cervix micrograph or photomicrograph image baselines for women so that image comparisons can be made from historical data if existing or cloud for general image processing and Electronic Medical Record, EMR, facilitation.

Yet another object of the invention is to use medical image technology for insitu exams processing live micrograph image data with stored digital images for online realtime diagnoses.

In the United States, the costs for pap test visits can cost, over $1,000, largely because additional tests are added that may or may not be necessary but prudent. Another objective if the invention is to rule in or out whether additional tests are necessary as proximate in time as possible after the Pap test, so that any additional tests or remedial actions can also be done directly alter the Pap test results are established in real-time.

Embodiments of the Invention

The Pap smear, not unlike many sampling methods, requires some bio-matter or sample to be removed from a patience by scraping an internal cavity, cervix, or surgical removal for placement on a glass slide for biopic and or microscopic evaluation. Automated image processing of sample slides exist from the more typical expert medical lab examiner. An aspect of the invention provides a "scraper" which removes surface and near surface tissue into an optical pocket equivalent to a slide sample complete with backlighting for an automated image examination insitu. The optical pocket is integrated with the components necessary for directing the wavelength or frequency light required at the timed trigger and image resolving durations for image magnifications as provided in lab slide sample analysis. The bio-sample scraper component integrated with the photonic components such as mirrors, beam splitters, fractionalized phase plates, laser/light fiber conduit channels, etalons, in-plane lasers or edge-emitting lasers which emit from surfaces, vertical cavity surface emission laser, VCSEL, and other photonic and digital components into a semi-rigid structure which can be inserted and selectively positioned so as to collect images from a sample in an optical pocket for obtaining in vivo magnified images without having to create external and extrinsic slide samples for image analysis or evaluation outside the cavity and with resulting delays in results.

The scraper stem carries optical fiber which functions as a waveguide, or "light pipe", to transmit light between the scraper optical flat plat surface and light source. The light source can be from a variety of sources as needed coming from LED, laser, tunable laser, UV, UVA, UVB, UVC, fluorescent and other very specific wavelength light. The scraper fiber stem provides illumination at a selected light wavelength to the optical paddle sample for backlight, or "condenser" light in a microscopy sense. The stem may be wrapped in fiber bundles so that separate or disparate wavelength light can be channeled in parallel or combination, thus allowing viewing and identifying harmful agents in low or no light confined spaces for different microbial matter. Some optical fiber can be used for a variety of other applications, including sensors and fiber lasers. In some embodiment many propagation paths or multi-mode fibers (MMF), or those that only support a single mode called single-mode fibers (SMF) are used for imaging for a variety of microbial matter.

Imaging and Microscopy

Analysis of bio-samples can depend the capability to focus on the depth at which the microbial or viral agents reside. Therefore selecting the optimal microscopy technology depends on a variety of factors.

Imaging depth is one of the most important microscopy optics considerations. Some biological processes occur at the surface, where cell membranes interact with their environments, while others happen deep beneath the surface. Specimen depth bio-matter at variable depth have must be accommodated. Light scatter, absorption, background signal, difficulty in collecting enough photons at the detector, and refractive index differences present a variety of challenges.

Various embodiments of the invention will have integrated components for a variety of optical path microscopes from Near Field Scanning (NFS), Stimulated Emission Depletion (STED), Photo Activated Localization Microscopy (PALM), Stochastic Optical Reconstruction Microscopy (STORM), Gated STED (gSTED), Fluorescence Correlation Microscopy (FCM), Time Tagged Time Resolved (TTTR), Confocal and other microscopy technologies for analysis insitu samples of biological or organic matter. Detector sensors and image production will be coupled with digital processing which can be local tool connected or wirelessly coupled to external processing and display devices.

Figure 1:
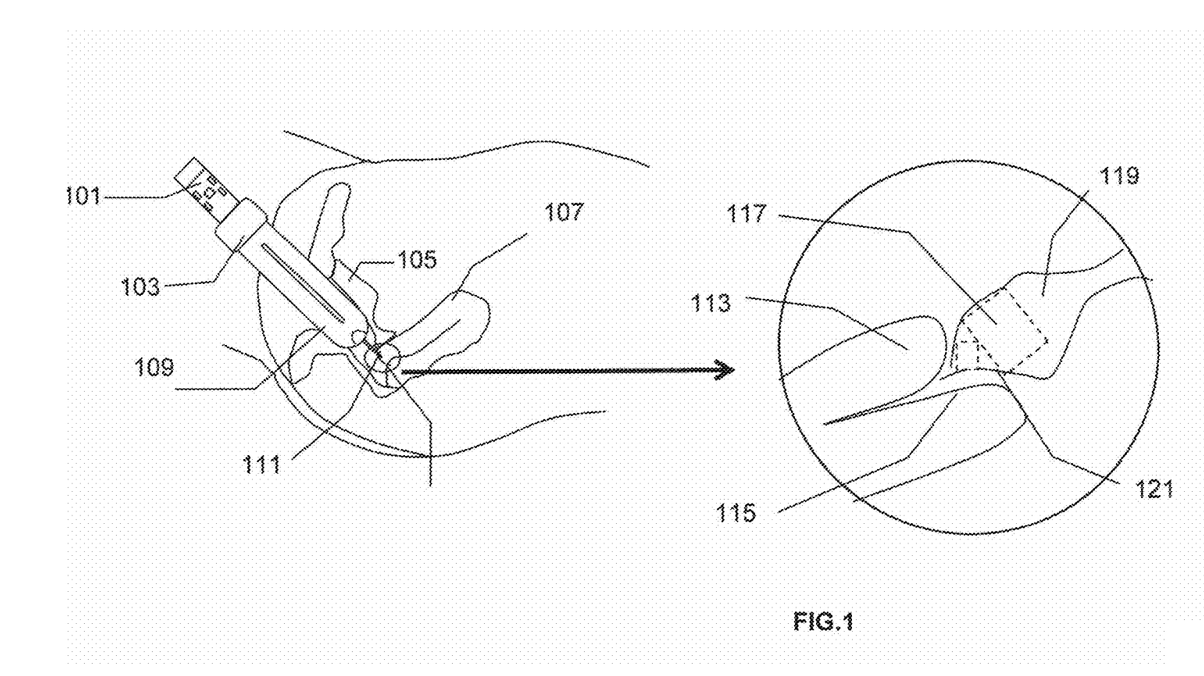
FIG. 1 is a cross sectional view of the in vivo environment and application for the tool according to the embodiment of the present invention.

FIG. 1 is a cross sectional view of the in vivo environment and application for the tool according to the embodiment of the present invention. A Pap smear bio-matter or sample is obtained from a patience by insertion of the tool 109 by tool handle 101 into the vagina cavity 105 up to a measurable position 103 for scraping a tissue sample from cervix 111, 113 which serves as the opening to the uterus 107. The opening to the cervix 115 provides a suitable position far the optical scraper 117 to enter and with a rounded or semi-rounded edge 121 scoop some tissue onto the optical scraper 119 pocket. In another embodiment of the invention the tool via a vaginal speculum or comparable tool to open the vaginal cavity for tool insertion.

Figure 2:
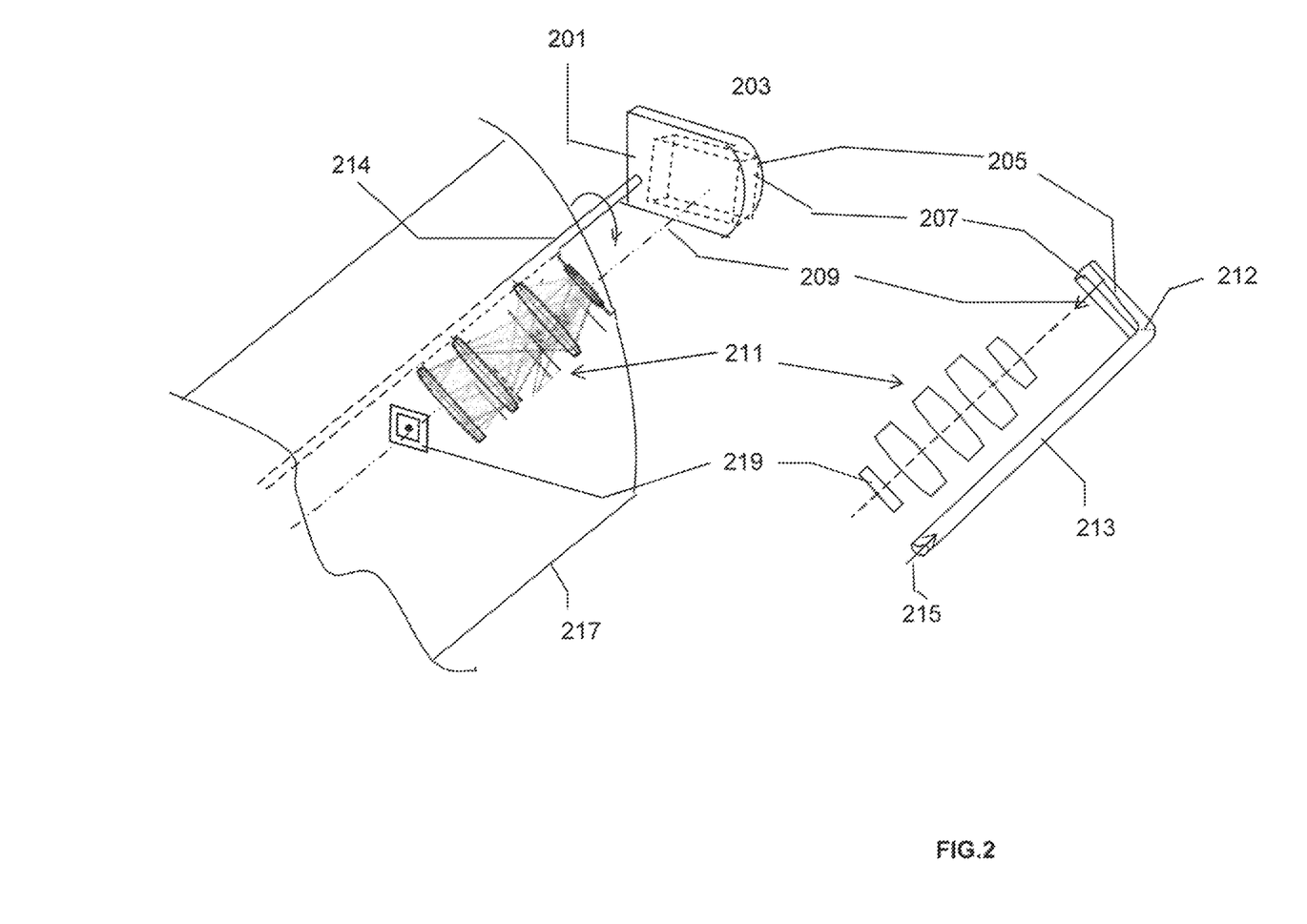
FIG. 2 is symbolic component illustration of a compound microscopy optical path through an vivo slide sample, according to the embodiment of the present invention.

FIG. 2 is representative component illustration of a compound microscopy optical path through an vivo slide sample, according to the embodiment of the present invention. In an embodiment tool housing 217 source light 215 is channeled in the stem 214 through optical fiber 213 or conductor across the scraper slide junction 212 and to the optical scraper far side 205. The scraper slide 201 has at least two sided, the far side 205 is furthest away from the optical lens 211 and the near side 207 is nearest the optical lens 207. Light is emitted from the normal scraper surface 209 through bio-matter scraped onto the near side surface 207 and into the microscope 211 optical path. The optically magnified object is focused onto the CCD or CMOS detector 219 which can then magnify the micrograph even further through electronic means. The optical path 211 illustrates a compound microscope serially with digital zoom. In other embodiments alternate microscopy optical/digital paths can be used. The scraper stem 214 is mechanically controlled to scrape a tissue sample and then retract to a good focal point position in front of the optical path front end lens.

In the simplest housing 217 embodiment a vaginal cavity conforming tool from various materials and construction. Silver is a germ resistant material and can also be used in an embodiment of the invention housing to retard or prevent material infection transfer. Other methods and materials can be used for the housing to ease cleaning and insure adequate disinfection of the tool.

In another aspect of the invention flexible OLED or AMOLED display on a silver grid housing may be used. A flexible display housing can be made from bendable plastic substrate, based on organic thin-film transistors (OTFTs), a main structure of the backplane made of polyethylene terephthalate (PET). In an embodiment of the invention a backplane can be laminated to a front plane, harnessing its electronic lighting display qualities technology with plastic logic's transistors, display with embedded light frequency LEDs in flexible substrate. In another embodiment flexible circuits electronic components are mounted on, or printed on, flexible plastic substrates, which can be made of polyether ether keytone (PEEK), an organic thermoplastic, polyimide, or transparent conductive polyester film.

Joining optical fiber channel to the scraper optical plate 201 portion must comply with the typical optical connectivity rules, whereby the ends of the optical fiber 212 must be carefully cleaved, and then carefully spliced together with the core alignment to the plate 201 while fusion splicing uses heat to fuse the ends of the fiber and plate slide scraper component together. Other optical fiber connectors for temporary or semi-permanent connections can be used and may include semi-conductor substrate material with optical properties such as plate embedded edge emitting lasers or diodes.

The total magnification is the product of: the objective lens magnification, the optics magnification and the enlargement factor of the display media. For some embodiments a compound microscopy optical path for simple optical and digital detectors magnification range is acceptable for a typical Pap smear micrograph.

In an embodiment of the invention the objective lens is, a very high powered magnifying glass i.e. a lens with a very short focal length. This is brought very close to the specimen being examined so that the light from the specimen comes to a focus about 160 mm inside the microscope tube. This creates an enlarged image of the scrape or smear sample. This image is projected onto the CCD or CMOS camera in line with the optical microscope. By carefully focusing a brightly lit specimen, a highly enlarged image is rendered onto the CCD or CMOS detector. It is this real image that is projected onto the detector that provides further enlargement, providing mechanism for digital zoom and focus on the virtual image. In other embodiments, images of different wavelength light can be detected using a multispectral line-scan camera. Mulitspectral filter optical components can be used for selected depths into a specimen sample, reconstructed post image processing. Optical coatings on the scraper slide paddle can facilitate the transmission of only certain wavelength light form certain image components.

Figure 3:
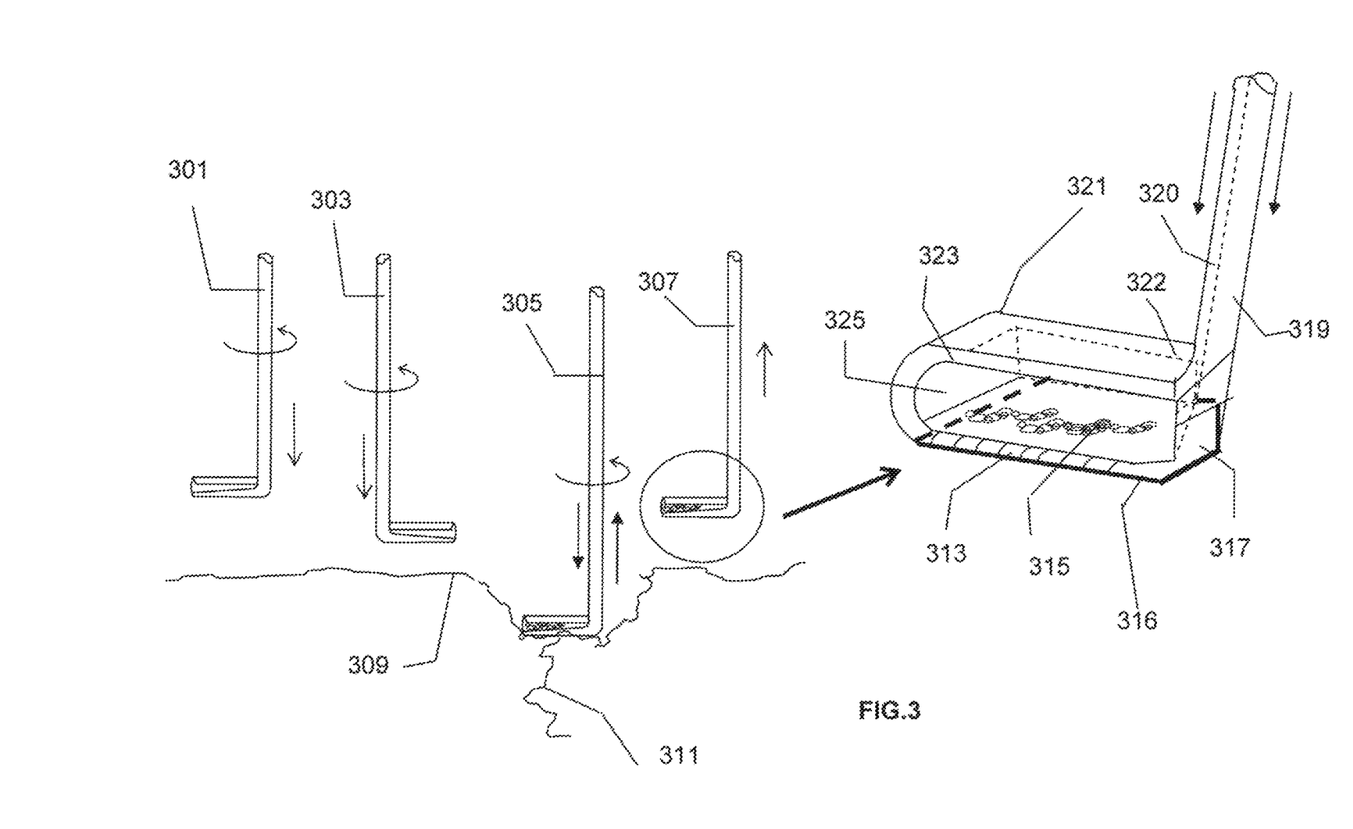
FIG. 3 is an illustration of a Pap optical scraper slide in vivo, according to an embodiment of the invention.

FIG. 3 is an illustration of a Pap optical scraper slide in vivo sample collection, according to an embodiment of the invention. A scraper 301 302 is inserted into the tissue 309 and pushed gently into the cervix 311 for sample collection. Some rotation and cervix opening in/out motion from the scraper stem motion will collect some tissue samples 315 onto the optical pocket 325. In an embodiment the scraper 321 will have smooth contoured leading edge 323 to better scoop bio-matter 315 onto the optical light pocket 325. A mirror 316 with high reflectivity may provide a layer on the scraper slide microscopy far side optical plate 313 to reflect and channel light into and through the slide bio-matter 315 collected in the optical pocket and onto the microscopy optical path normal to the optical scraper 321 surface plane. Laser/light is conducted through fiber 319 stem and into to optical scraper paddle, for light emission through the scraped bio-matter 315 sample. In an embodiment of the invention a rangefinder and control logic or proximity sensor guides the scraper paddle to the target and upon sample recovery returns the optical scraper paddle component to the tool focal plane for imaging.

In an embodiment of the invention surface emitting LED or Semiconductor Laser light from the slide surface is channeled through the optical plate scraper far side 317. In some embodiments of the invention the scraper optical slide far side 317 will have surface-emitting semiconductor lasers providing backlight. These can be in the form of vertical cavity surface-emitting laser, VCSEL, optically or electrically pumped output beams. For higher output power vertical external cavity surface-emitting lasers, VECSELs, can also be used along with other surface emitting laser/light technologies. In another embodiment of the invention vertical emission of light from the scraper slide surface can also be achieved with a edge emitting laser diode which is based on a waveguide along the chip surface as in an edge-emitting laser. Here light emission is in the vertical direction because the light is reflected upward with a 45° mirror, horizontal cavity surface-emitting laser, HCSEL. In another embodiment, more than one laser/light channel 320 will emit conducted multi-wavelength light through the sample for various microscopy effects.

Figure 4:
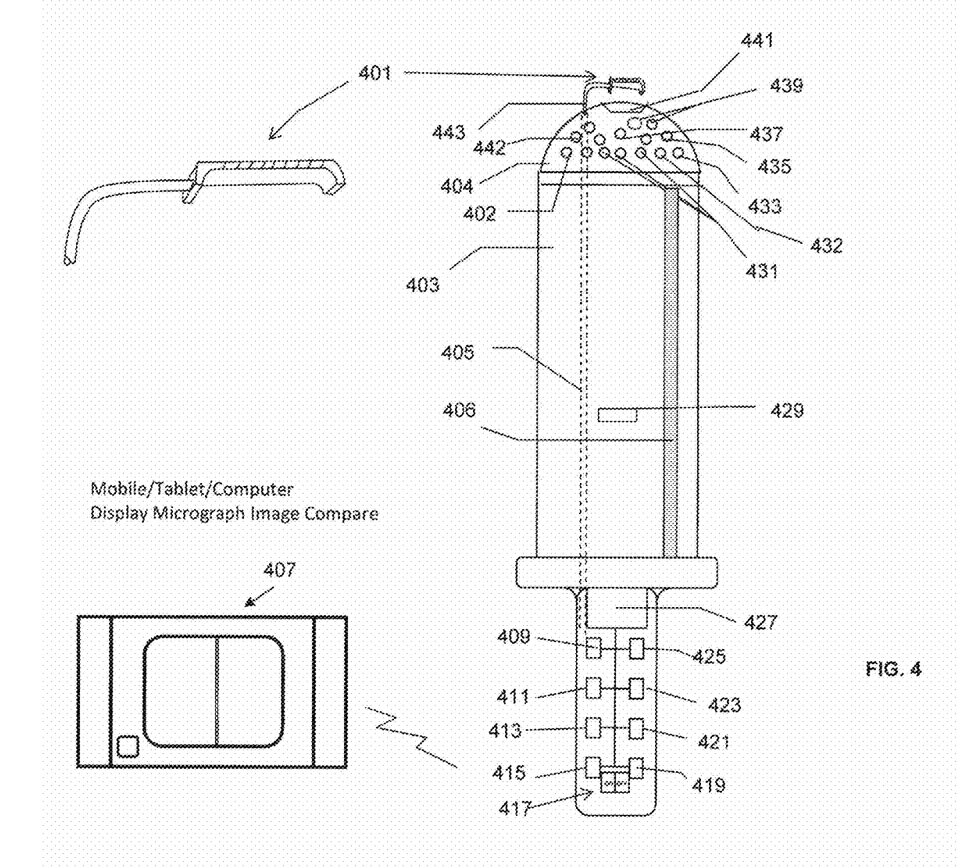
FIG. 4 is a component view of an in vivo diagnostic and tool according to an embodiment of the invention.

FIG. 4 is a component view of an in vivo diagnostic tool according to an embodiment of the invention. A housing 403 contains the components of the tool, extended from a handle 417 and ending in a top 404 outer portion from which an optical scraper optical pocket slide 401 coupled to an optical property stem 405 which can be extended outward from the housing 403 upon command. In an embodiment the stem 405 optical property can be a mono or multi-wavelength multimode fiber channel. In an embodiment an object optical lens 441 leading a set of lenses providing a microscopic optical magnification is aligned along an optical path normal to the scraper slide 401 surface. In another embodiment scattered light detectors 439 or 3D detector lens are positioned on the head 404. In yet other embodiments laser 435, proximity sensor or rangefinder 432, excitation laser 437, fluorescence laser 433 and or variable frequency LED array light sources are positioned on the tool head 404. An optical path through the optical lens set is focused onto an image detector CCD 429. The image detector CCD or CMOS is electronically coupled to components and logic to process the image micrographs including program logic 409, memory 425, image processor 411, image storage 423, image comparator 421, CPU 413, wireless chip set 415 and power 417. The wireless chip set 415 and logic 415 409 facilitate wireless I/O to-from a mobile, tablet or computer 407 for display and more. In another embodiment, a CCD or CMOS imaging array 406 detector extends along the longitudinal housing to provide a cavity length dimension image or video sample. An intense CMOS multiplier or photonic counting CCD may be used in embodiments where illumination is expected to be extremely low. A small window touch screen display 427 will provide control selections for verification, confirmation and basic user interface commands.

In an embodiments of the housing 403 the dimensions will be such that the tool will be inserted in vivo through a speculum. In some embodiments the housing outer material will be physically compatible with human tissue and human cells, capable of adequate cleaning, disinfection and sterilization processing.

Various sources of light can be used in microscopy embodiments depending on requirements for the microscopy optical paths applied. In a simple embodiment, visible lamp light, multi-wavelength, LEDs or laser light will illuminate the target "sample" by conducted mono or multimode fiber optic light to an optically conductive Pap tissue scraper paddle having surface emitting optical character. The scraper paddle light is conducted from the scraper stem and through the paddle scraper far surface. This scraper portion has optical properties for the photonic functions but can also be of semi-conductor material for enhancing emission of laser light through its normal surface, providing a light source serving as the condenser backlight traveling through a specimen on the scraper surface.

In another embodiment of the invention, far side of the optical scraper slide has a reflecting mirror on the scraper paddle far side reflecting any internal light back towards the near paddle surface containing the sample. This optical scraper paddle surface 401 emits backlight through the microscope specimen acting as a "condenser" lens designed to focus light from the illumination source onto the specimen scraped from the tissue wall onto the optical scraper surface or pocket. The optical scraper "condenser" may also include other feature as such as a diaphragm and/or filters, to manage the quality and intensity of the light in the cavity visited, here the vagina towards the end adjacent and centered on to the cervix opening. For special illumination techniques, additional optical components must be precisely aligned in the light path from the specimen to the objective lens 441, pin hole 442 or photon counting/imaging detector 402. Some invasive cancers can penetrate the tissue making them undetectable to visible inspection. Fluorescent biomarkers can help reveal these. Photon counting and imaging provides an alternate capability where the scattered or reflected extremely low-light conditions require some tissue penetration. ICCD or EMCCD image detectors would convert the photons to electrons and then back to photons for counting purposes in the total internal reflection fluorescence, TIRF, optical path. These light sources can be positioned on the housing distal end having internal cavity projected light sources from laser, IR, UV and LED for accommodating disparate scattered light microscopy optical paths.

In an embodiment of the invention the actual power or magnification of a compound optical microscope is the product of the powers of the ocular and the objective lens. The maximum normal magnifications of the ocular and objective are 10× and 100× respectively, giving a final magnification of 1000× not including the digital power magnification.

An inline CCD or CMOS camera with pixel size and number of the pixels in the detector provide yet another enlargement factor. A typical Pap stained cervical cell image, acquired through a CCD camera adapted to an optical microscope will require at least a 40× magnification lens and images stored in JPEG format having size 2048×1536 pixels. Digital magnification will be 5×-20× and the enlargement factor approx 5×. So the optical magnification of 40× means that smaller optical path and girth dimensions are within the housing or human cavity range.

Figure 5:
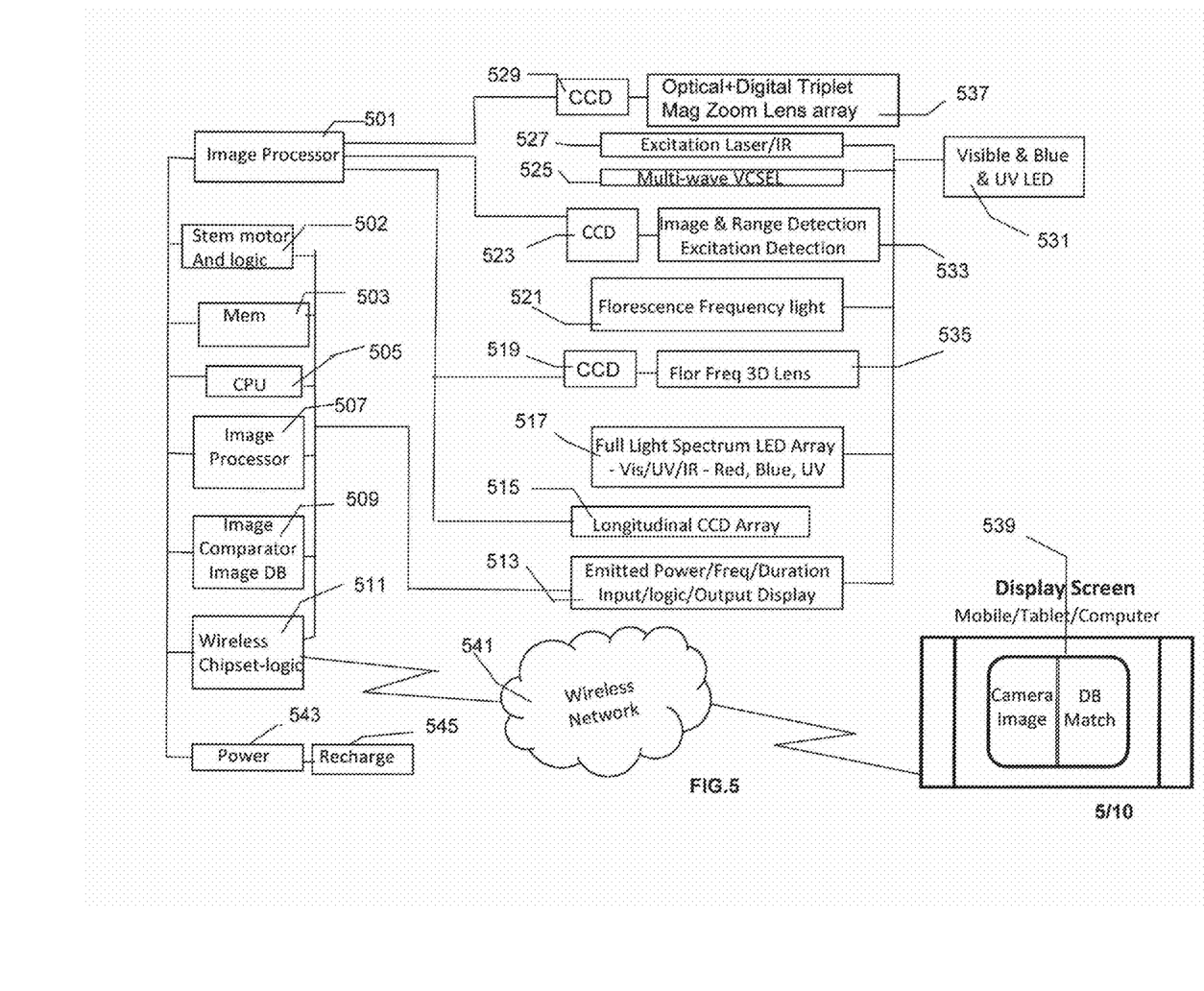
FIG. 5 is component block diagram of an in vivo diagnostic tool according to an embodiment of the invention.

FIG. 5 is component block diagram of an in vivo diagnostic and light therapy tool according to an embodiment of the invention. There are at least two different aspects to the laser/light sources. The first is for illumination of in vivo obtained slide samples or targets from the cervix through back lighting, substitution of the lab microscope condenser with the scraper optical paddle. The second major feature is the illumination or exposure of the tissue from above without use of the scraper tool but with microscopy optical path methods using scattered light.

An embodiment of the invention can contain some or all of the electronic components including CCD image input processing 501, motor control logic 502 of the stem for sample collection and focal plane positioning, basic computer memory 503, a control program executing CPU 505, image formatting processor 507, image real-time depth composition and high frame rate scans through a focal range of a sample to recognize areas of focus to build a fully-focused image programmatically, image comparator with stored image library or downloadable image micrographs which in some embodiments can include laser/light frequency/duration/power requirements for therapy application. Couple with the electronic components of an embodiment are wireless chip set 511 using any available wireless protocol to a wireless network 541. Power 543 source and/or recharging 545 capabilities provide electrical power to the tool.

In an embodiment of the invention applying laser/light sourcing from a tunable laser may be used. CO2 laser has been used to treat cervical squamous intraepithelial lesions (SILs). In an embodiment of the invention, after confirmation with a cervical biopsy Image micrograph, appropriate therapy light treatment for a beam of infrared light with the principal wavelength bands centering around 9.4 and 10.6 micrometers can be applied. The tunable frequency laser having CW powers in milliwatts, mW, can be used. A laser producing a beam of UV or infrared light with the principal wavelength bands centering around 9.4 and 10.6 micrometers are integrated in some embodiments to identify some SILs.

In laser or light source aspect embodiments, to determine the laser power density output requirements, one method is to calculate the area over which the laser/light will distribute power, milliwatts, and programmatically insure that the illumination delivered to the target area is below allowable and set power applications. In some embodiments this will be automated in logic and in other embodiments physicians will be provided flexibility in applying alternate microscopy methods to an individual and specific patient. If the laser is calibrated to a known intensity, millWatts-mW, in continuous mode, the target size can easily be adjusted to provide the proper power density by positioning the laser light source. A camera image without magnification can be used to ascertain the exact area for application and the power therapy requirements can be from known data and local geometry, for optimal illumination over a specific area. The three factors to be considered in the laser/light source are the 1) laser power, 2) length of time for which the laser intensity acts, and 3) area size on the tissue. Knowing the laser power and the area subtended, the time can be calculated and set by default for an automatic programmed pulse working in concert with image intermittent takes. CCD imaging logic can be used with Time Tagged Time Resolved (TTTR) methods to obtain yet liner images for smaller entities.

Different bio-entities of different size, scope and range dictate that several laser/light sources and modes be available for the tool optical path. In some embodiments one or more laser/light sources including an Excitation Laser/Infra Red 527, Multi-wave VCSEL 525, Fluorescence frequency light 521, full light spectrum LED array 517 for visible-Red, Blue/UV/IR frequency light are available sources.

Detectors and sensors include and optical/digital triplet magnification zoom lens array with CCD or CMOS 529, Image, range detection and excitation detection with CCD 523, Fluorescence frequency 3D lens set and CCD 519, longitudinal CCD array 515 detector for a cavity length wise scan. The housing may have a power/frequency/duration output display from control logic 513 for the emitting laser/light 527, 525, 521, 517 light sources. The wireless 511 connectivity will have display screen 439 variability to mobile/tablet or computer screens.

Figure 6:
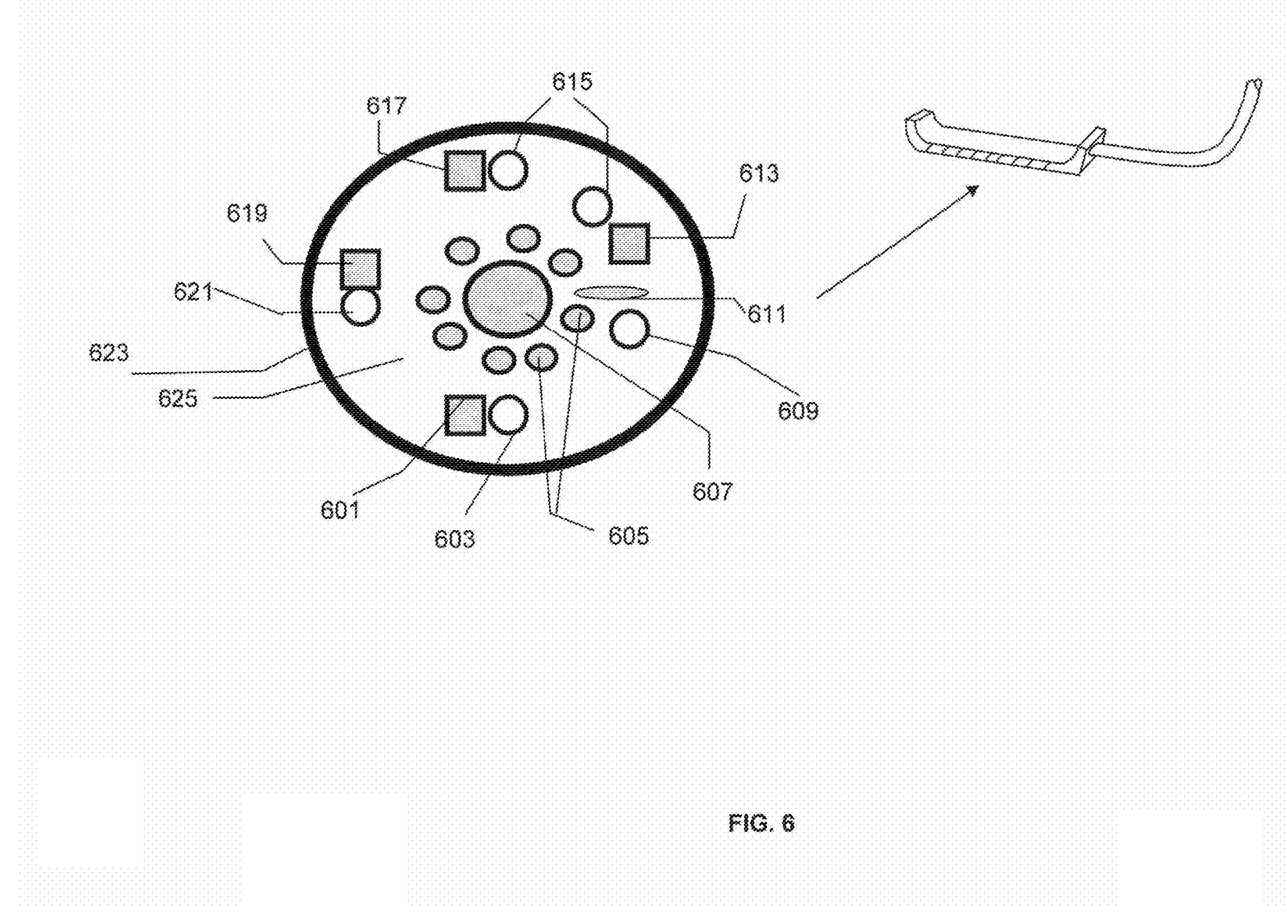
FIG. 6 is an front view illustration of an in vivo diagnostic tool according to an embodiment of the invention.

FIG. 6 is a front view illustration of an in vivo diagnostic tool according to an embodiment of the invention. The tool housing 623 has an internal cavity facing end 625 which contains an integration of detectors and laser/light sources. An optical lens 607 resides in the optical path center and is surrounded by an array of various frequency LEDs 605. An optical scraper slide opening 611 for an extendable optical scraper aspect of the invention which provides an in vivo specimen on a "slide" for microscopic scrutiny and image magnification. Other optical return paths 609 may be offset for other microscopy methods such as NFS, STED, PALM, STORM, gSTED, FCM, TTTR, Confocal and other microscopy technologies. For this and other reasons various frequency LEDs outwardly facing may include UV-C 603, UV 621 and or with laser 617 613 601, IR 615 at various locations for reaching determined areas subtended.

Figure 7:
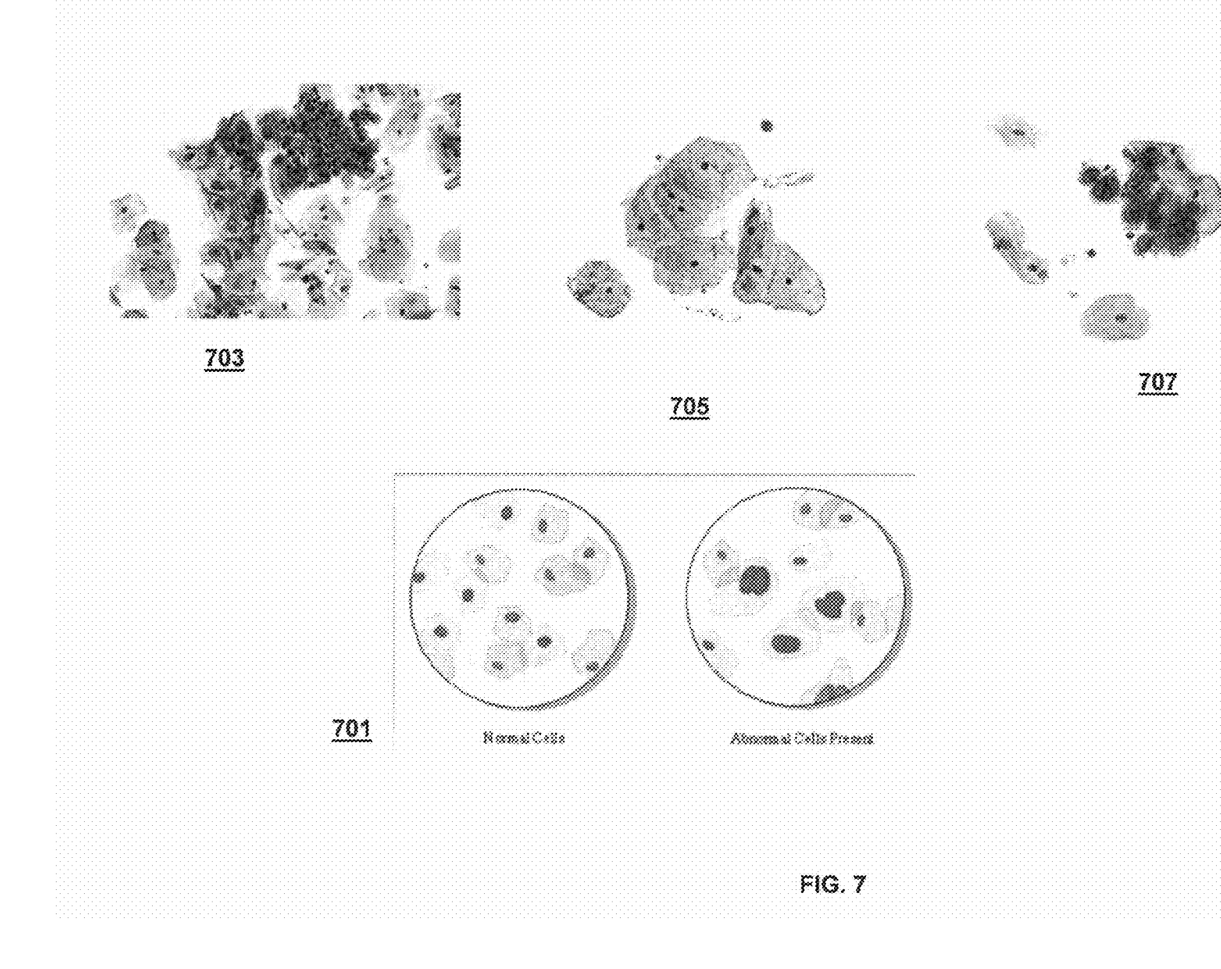
FIG. 7 illustrates in vivo images for bio specimen comparison analysis of abnormalities for in vivo diagnostic tool according to an embodiment of the invention.

FIG. 7 illustrates in vivo images for comparison analysis and identification of collected sample abnormalities for in vivo diagnostic tool according to an embodiment of the invention.

Image analysis begins with obtaining a digital micrograph of a specimen for comparison with stored known images of lesions, and other abnormalities or harmful agents. Optical scraper or probe obtained micrographic images are processed by image analysis and compared against known images for identification and potential hazards. Images are sent for analysis against local or remote image stored and compared for Pap micrographs showing low-grade intraepithelial lesion (LSIL) 703 and benign endecervical mucosa. *Trichomonas* organism 705, herpes simplex virus 707, and any of the known precancerous or cancerous HPV variants in the form of normal to abnormal cell 701 micrographs.

The step of identification of harmful agents provides obtaining an image of the offending microbial specimens including Endocervical adenocarcinoma, Candide organisms, viral cytopathic effect consistent with herpes simplex virus, normal squamous epithelial cells in premenopausal women, atrophic squamous cells in postmenopausal women, the cytoplasms of squamous epithelial cells melted out, Infestation by *Trichomonas vaginalis*, obviously atypical cell, HPV legions and other anomalous or symptomatic characteristics, legions, anomalous growth. Identification of the offenders requires creation of micrograph images of different bio-matter sizes, different magnification, and sometimes in different depth in the tissue. Detection therefore accounts for all of these but in some embodiments the scale and scope of the tool will determine which biological entity is sought.

In addition to the typical Pap smear bio-matter of diagnostic import are sexually transmitted diseases. These including *Chlamydia trachomatis, Neisseria gonorrhoeae, Treponema pallidum, Ureaplasma urealyticum, Haemophilus ducreyi* and other such bio-entities are prime imaging diagnostic candidates. Urinary tract infections including *Escherichia coli*, other *Enterobacteriaceae, Staphylococcus saprophytics, Pseodomonas aeruginosa* are more bio-entities which are potential image diagnostic bio entities for identification for remedial treatment.

Laser-based imaging is relatively incorporated into an aspect of the invention. Laser based imaging embodiment provides a combination of non-toxic gold nano particles and light to viscous specimens containing mucus or mucus like substances to obtain better images. In an embodiment of the invention specimen viscosity-thinning agents can be placed in or on the optical scraper paddle surface for improving specimen flow and specimen image collection.

Figure 8:
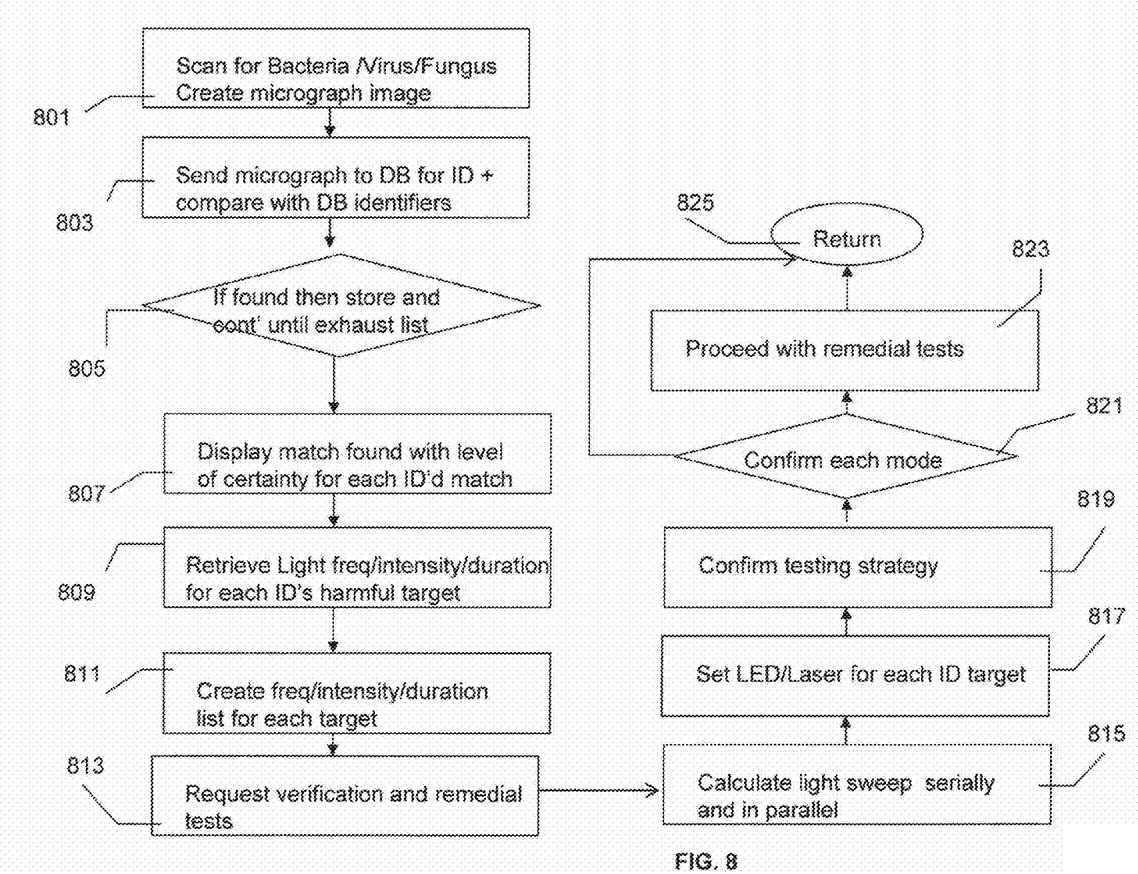
FIG. 8 is a process block diagram for in vivo diagnosis tool according to an embodiment of the invention.

FIG. 8 is an process block diagram for in vivo diagnosis tool according to an embodiment of the invention.

Diagnosis for harmful agent targets includes a series of steps for ascertaining harm for remedial subsequent action. A scraper specimen or probe image scan 801 must be made to create the micrograph image for detection. The optical image is then transferred to digital 803 to obtain specimen micrograph which can be compared against locally stored or remotely stored images. For efficiency, a plurality 805 of micrographs can be made to identify one or more harmful agent targets. Many digital image processing algorithms exist and are currently employed in identifying harmful agents, some more common are shown in FIG. 7. The micrograph image can be displayed and or stored when matches are found 807. In subsequent remedial modes, sequence for each identified match are retrieved from the a database or library 809. Order and the number of runs 811, serial or parallel threat removal, is programmed in to cover all match threats in a programmed sequenced light scans 815 after confirmation 813 and verification, where possible and in series where resources collide. In an embodiment of the invention an endoscope can be integrated into a optical stem to facilitate some procedures of obtaining an image and identifying the targets. A final confirmation 819 may be required by the physician.

An abbreviated step sequence implements a variable Light frequency programmable for targets method using computer pattern matching images with known micro entities includes the steps of: 1) Scan and Identify the harmful target images, 2) obtain image and send for ID match in library database (DB), 3) compare with DB specimens, 4) Display found matching image on screen, 5) request type of light therapy required upon confirm at programmed power/freq/duration.

Figure 9:
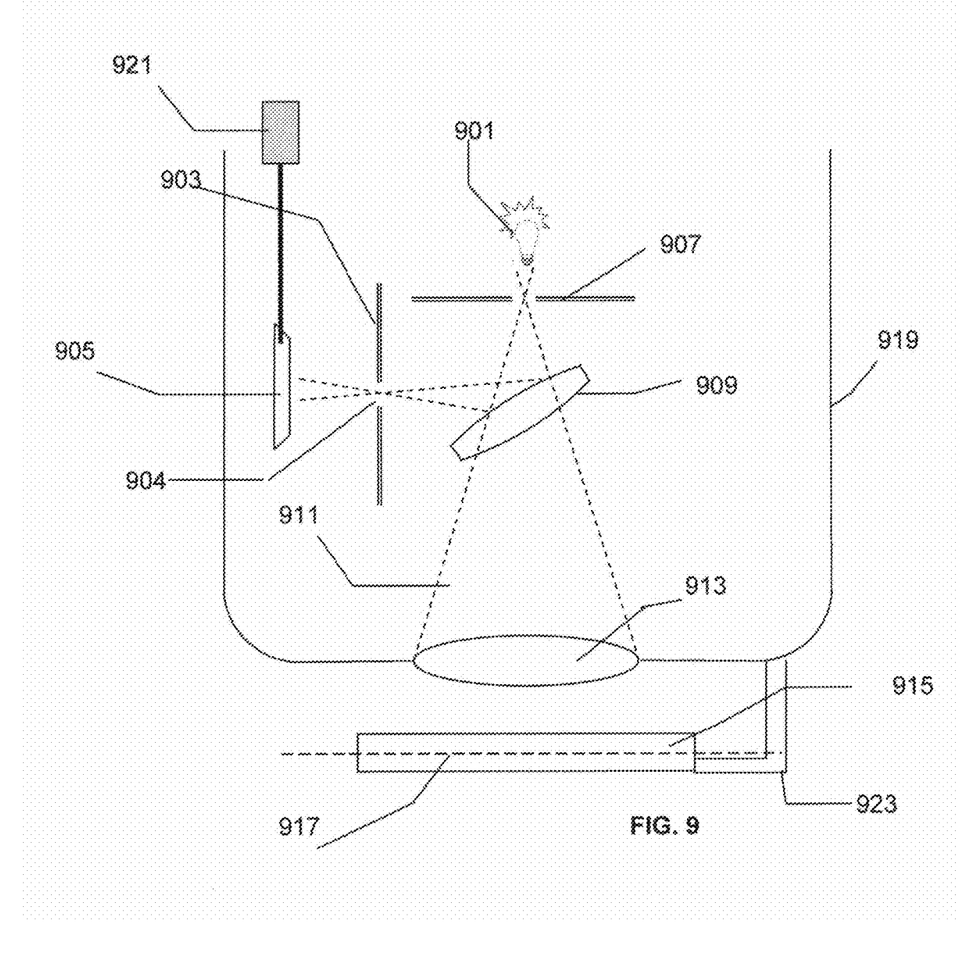
FIG. 9 is component level illustration of a confocal optical path of an in vivo diagnostic according to an embodiment of the invention.

FIG. 9 is component illustration of a confocal optical path of an in vivo diagnostic and light therapy tool housing 919 according to an embodiment of the invention.

Confocal microscopy imaging embodiment is yet another optical imaging path for increasing optical resolution and contrast of an in vivo micrograph by means of adding a spatial pinhole 994 placed at the confocal plane 903 of the lens 909 to eliminate out-of-focus light.

A confocal microscope configuration embodiment uses point illumination and a pinhole 904 aperture in an optically conjugate plane 909 in front of the detector to eliminate out-of-focus signal. The optical path 911 is channeled through a beam splitter 909 and into the detector 905 via aperture 904. As only light produced by fluorescence very close to the focal plane 917 can be detected, the image's optical resolution, particularly in the sample 913 depth direction, is much better than that of wide-field microscopes. The stem 923 is position controllable from control logic coupled to mechanical motion controls and range finder input for focal plane focusing.

In an embodiment, points in the sample 915 on the optical scraper slide are illuminated sequentially. 2D or 3D imaging requires scanning over a regular raster CMOS or CCD 905, a rectangular pattern of parallel scanning lines, in the specimen 915, is then transmitted to the CCD 905 image processor 921. The achievable thickness of the focal plane 917 is defined mostly by the wavelength of the used light 901 divided by the numerical aperture 903 of the optical lens 913, but also by the optical properties of the specimen 915 on slide supported on the scraper stem 923. The light source 901 can be LED or tunable laser to provide the optimal wavelength required. In another embodiment the sample specimen 915 can be in vivo tissue and focal plane 917 can be the tissue surface or a depth within the in vivo tissue.

Figure 10:
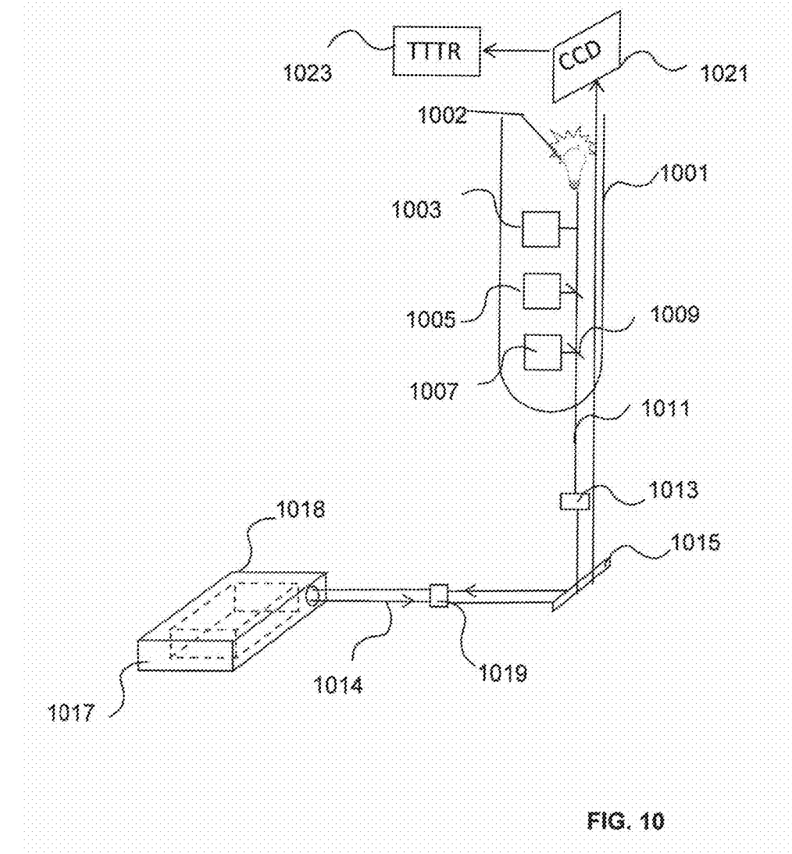
FIG. 10 is symbolic component level illustration of a TIRF optical path of an in vivo diagnostic tool according to an embodiment of the invention.

FIG. 10 is symbolic component illustration of a TIRF optical path of an in vivo diagnostic and light therapy tool according to an embodiment of the invention.

In another embodiment, smaller organic entities or bio-molecules requiring identification and examination of proteins in vivo will dictate higher power magnification or even lower illumination conditions. In some embodiments digital imaging detection such as Intensive CCD or Electron Multiplying CCD, may thus substitute for some optical path embodiment components providing images to the detector CCD 1021, ICCD, sCMOS or EMCCD, where prescribed for extremely low-light higher powers and resolutions using the optical configuration for Total internal Reflection Fluorescence, TIRF. These in turn call for high-intensity laser to trigger molecular fluorescence. In another embodiment where added sensitivity of the camera is required, EMCCD 1021 photo counting imaging microscopy complete with optical path embodiments can be implemented. In yet another embodiment a Total Internal Reflection Fluorescent Microscope, TIRFM, is used sourcing an evanescent wave 1002 to illuminate and excite fluorophores on the slide surface 1018 when the incident light is totally internally reflected from the scraper slide surface 1018, penetrating to a select, sample depth and returning signal In a parallel return path 1014 eventually to the detector 1021.

In other embodiments the optical path may require further optical and electronic components in the optical channel beginning with a light source 1002, excitation laser 1005, STED 1007, and single or multi-mode fiber channel 1011, a quarter-wave plate, dichroic mirror(s) 1009 1015 for frequency selection and filtering, segmented phase plate 1019, sample slide glass 1017 and return signal path 1014 to a detector 1021 and timed processing, TTTR, 1002. Logic and motor control 1003 of the optical scraper plate is needed for obtaining desired in vivo sample specimens Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. An insitu bio-matter imaging diagnostic tool comprising:
 a housing having an optical and digital magnification path coupled to image detecting sensor and logic,
 a scraper slide configured to scrape cells from tissue and to hold the cells for examination,
 an optical scraper stem mechanically controlled and extendable from the housing and configured to hold the scraper slide, the stem having at least one fiber optic channel for conducting selected frequency and wavelength light from single wavelength or tunable wavelength light sources,
 an optical scraper slide component optically coupled to the optical scraper stem distal end, channeling light from the housing to the scraper slide normal axis surface for illumination penetrating a specimen sample for optical imaging into an optical microscopy magnification path axis,
 the optical microscopy magnification path magnifying and focusing micrograph images on the image detecting sensor being a digital CCD or CMOS detector,
 the image detecting sensor electronically coupled to electronic imaging programmatic processing and display of micrograph images,
 the image programmatic processing coupled to logic for digital image comparison and identification of known harmful or precursors to harmful bio-matter in the micrograph image, and
 display of image processing results locally or on remote digital display device,
 whereby image comparisons can be accomplished and resulting digital image micrographs from optical scraper collection programmatically processed, harmful agents identified and verified in situ in real-time.

2. The insitu diagnostic tool as in claim 1 further comprising logic for programmatically selecting and controlling intensity, frequency and power light sources which can be directed onto insitu targets identified for the micrograph image processing.

3. The insitu diagnostic tool as in claim 1 further comprising coupled local and wireless remote components for display of scraper micrographs and identified matching images, displays from a set of displays consisting essentially of mobile, tablet, phablet, computer screen, and local tool small window.

4. The insitu diagnostic tool as in claim 1 wherein the optical microscopy magnification path is selected from a group of microscopy optical paths including single lens, compound lens, confocal, TIRFM, Photonic, and Fluorescent.

5. The insitu diagnostic tool as in claim 1 further comprising a coupled optical window transparent to selectable wavelength light from a group of light sources consisting essentially of visible, red, blue, UV-A, UV-B, UV-C, LED, excitation laser, fluorescent, full spectrum, multi-wave and Infra Red.

6. The insitu diagnostic tool as in claim 1 further comprising scraper side normal to the surface emitting light from a set of surface emitting light components consisting essentially of VCSEL, VXSEL, edge emitting laser diode, surface laser, internal mirror.

7. The insitu diagnostic tool as in claim 1 further comprising a video capture and storage component for video in situ images.

8. The insitu diagnostic tool as in claim 1 further comprising the housing distal end having internal cavity projected light sources from a set of light sources consisting essentially of laser, IR, UV and LED for accommodating disparate scattered light microscopy optical paths.

9. The insitu diagnostic tool as in claim 1 further comprising the optical microscopy magnification path for image capture longitudinally and circumferentially in the in vivo cavity.

10. The insitu diagnostic tool as in claim 1 further comprising a local image library or remote wireless accessible database of bio micrographs and logic for image matching identification and Electronic Medical Record management.

* * * * *